United States Patent
Davidson

(10) Patent No.: US 10,070,777 B2
(45) Date of Patent: Sep. 11, 2018

(54) SYSTEM AND METHOD FOR DISPLAYING AN IMAGE STREAM

(71) Applicant: GIVEN IMAGING LTD., Yoqneam (IL)

(72) Inventor: Tal Davidson, Yoqneam Illit (IL)

(73) Assignee: Given Imaging Ltd., Yoqneam (IL)

( * ) Notice: Subject to any disclaimer, the term of this patent is extended or adjusted under 35 U.S.C. 154(b) by 636 days.

(21) Appl. No.: 14/618,199

(22) Filed: Feb. 10, 2015

(65) Prior Publication Data

US 2015/0196195 A1 Jul. 16, 2015

Related U.S. Application Data

(63) Continuation of application No. 13/279,515, filed on Oct. 24, 2011, now Pat. No. 8,982,205, which is a continuation of application No. 12/323,620, filed on Nov. 26, 2008, now Pat. No. 8,045,000, which is a continuation of application No. 10/610,915, filed on Jul. 2, 2003, now Pat. No. 7,474,327, which is a continuation-in-part of application No. 10/364,508, filed on Feb. 12, 2003, now Pat. No. 7,505,062.

(60) Provisional application No. 60/355,796, filed on Feb. 12, 2002.

(51) Int. Cl.
- *H04N 9/47* (2006.01)
- *A61B 1/04* (2006.01)
- *A61B 1/00* (2006.01)

(52) U.S. Cl.
CPC ............ *A61B 1/041* (2013.01); *A61B 1/0005* (2013.01); *A61B 1/00045* (2013.01)

(58) Field of Classification Search
CPC .. A61B 1/041; A61B 1/00009; H04N 3/2335; H04L 12/44; G06F 19/321; G06T 15/20
USPC .......................................................... 348/77
See application file for complete search history.

(56) References Cited

U.S. PATENT DOCUMENTS

| | | | |
|---|---|---|---|
| 4,862,388 A * | 8/1989 | Bunker | ................... G06T 15/20 345/427 |
| 4,907,095 A | 3/1990 | Komura et al. | |
| 5,566,169 A * | 10/1996 | Rangan | ................... H04L 12/44 370/352 |
| 5,605,153 A * | 2/1997 | Fujioka | ................. G06F 19/321 382/128 |
| 5,726,670 A | 3/1998 | Tabata et al. | |
| 5,880,777 A | 3/1999 | Savoye et al. | |
| 6,289,165 B1 | 9/2001 | Abecassis | |
| 6,367,933 B1 * | 4/2002 | Chen | .................... H04N 3/2335 348/744 |
| 6,504,990 B1 | 1/2003 | Abecassis | |
| 6,904,308 B2 | 6/2005 | Frisch et al. | |
| 7,272,657 B2 | 9/2007 | Allen et al. | |
| 7,324,673 B1 | 1/2008 | Yamanaka et al. | |

(Continued)

FOREIGN PATENT DOCUMENTS

JP 2000047651 2/2000

*Primary Examiner* — Gims S Philippe
(74) *Attorney, Agent, or Firm* — Pearl Cohen Zedek Latzer Baratz LLP

(57) ABSTRACT

A system and method may display an image stream, where an original image stream may be divided into two or more subset images streams, each subset image stream being displayed simultaneously or substantially simultaneously. The images may be displayed fused. The images may be collected from an ingestible capsule traversing the GI tract.

13 Claims, 12 Drawing Sheets

(56) References Cited

U.S. PATENT DOCUMENTS

| | | | |
|---|---|---|---|
| 7,724,928 B2* | 5/2010 | Glukhovsky | A61B 1/041 |
| | | | 382/128 |
| 2002/0140861 A1 | 10/2002 | Janevski et al. | |
| 2002/0177779 A1* | 11/2002 | Adler | A61B 1/00009 |
| | | | 600/476 |
| 2003/0086596 A1 | 5/2003 | Hipp et al. | |
| 2003/0174208 A1 | 9/2003 | Glukhovsky et al. | |
| 2006/0164511 A1 | 7/2006 | Krupnik | |

* cited by examiner

SYSTEM AND METHOD FOR DISPLAYING AN IMAGE STREAM

CROSS-REFERENCE TO RELATED APPLICATION

This application is continuation of patent application Ser. No. 13/279,515, filed Oct. 24, 2011, entitled "System and Method for Displaying an Image Stream, which is continuation of patent application Ser. No. 12/323,620, filed Nov. 26, 2008, which in turn is a continuation of patent application Ser. No. 10/610,915, filed Jul. 2, 2003, entitled "System and Method for Displaying an Image Stream", which in turn is a continuation-in-part of patent application Ser. No. 10/364,508, filed Feb. 12, 2003, entitled "System and Method for Displaying an Image Stream", which in turn claims the benefit of provisional application No. 60/355,796 filed Feb. 12, 2002 entitled "System and Method for Viewing a Moving Image", each of which are incorporated by reference herein in their entirety.

FIELD OF THE INVENTION

The present invention relates to a method and system for displaying and/or reviewing image streams. More specifically, the present invention relates to a method and system for effective displaying of an image stream.

BACKGROUND OF THE INVENTION

An image stream may be assembled from a series of still images and displayed to a user. The images may be created or collected from various sources. For example, U.S. Pat. No. 5,604,531 to Iddan et al., assigned to the common assignee of the present application and incorporated herein by reference, teaches an in-vivo imager system which in one embodiment includes a swallowable capsule. The imager system captures images of a lumen such as the gastrointestinal (GI) tract and transmits them to an external recording device while the capsule passes through the lumen. Large numbers of images may be collected for viewing and, for example, combined in sequence. An image stream of, for example, 40 minutes in length, containing for example about 4,800 frames, may be presented to the user for review. Other numbers of frames or lengths may be used. In one embodiment, a streaming rate is preset, but the user can increase or decrease the streaming rate at anytime during the review process, and/or define a different streaming rate. In general, a user may try to set the streaming rate to the highest rate where the user can quickly and effectively review the image stream without missing important information that may be present in any of the images included in the stream. The rate at which a user can effectively review a image stream is limited by a physiological averaging effect that is known to exist at around 15 frames per second (although this number varies for different users and image streams) above which certain details in individual images displayed in the stream may be physiologically filtered out.

Therefore, a need exists for a system and method that enables a user to increase the rate at which the user can efficiently and effectively review an image stream.

SUMMARY OF THE INVENTION

In one embodiment, a system and method are provided for displaying an image stream, where an original image stream is divided into two or more images streams, each image stream being displayed simultaneously or substantially simultaneously. According to another embodiment of the invention, two or more subset image streams are displayed simultaneously or substantially simultaneously as a single entity stream.

When used herein, "substantially simultaneously" includes simultaneously and almost simultaneously. A system and method according to one embodiment of the invention enables a user to see images in the stream for a longer period of time without increasing the overall viewing time of the entire image stream. Alternatively, the system and method described according to one embodiment may be used to increase the rate at which a user can review the image stream without sacrificing details that may be depicted in the stream. In certain embodiments, the images are collected from a swallowable capsule traversing the GI tract.

BRIEF DESCRIPTION OF THE DRAWINGS

The present invention will be understood and appreciated more fully from the following detailed description taken in conjunction with the drawings in which.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1:
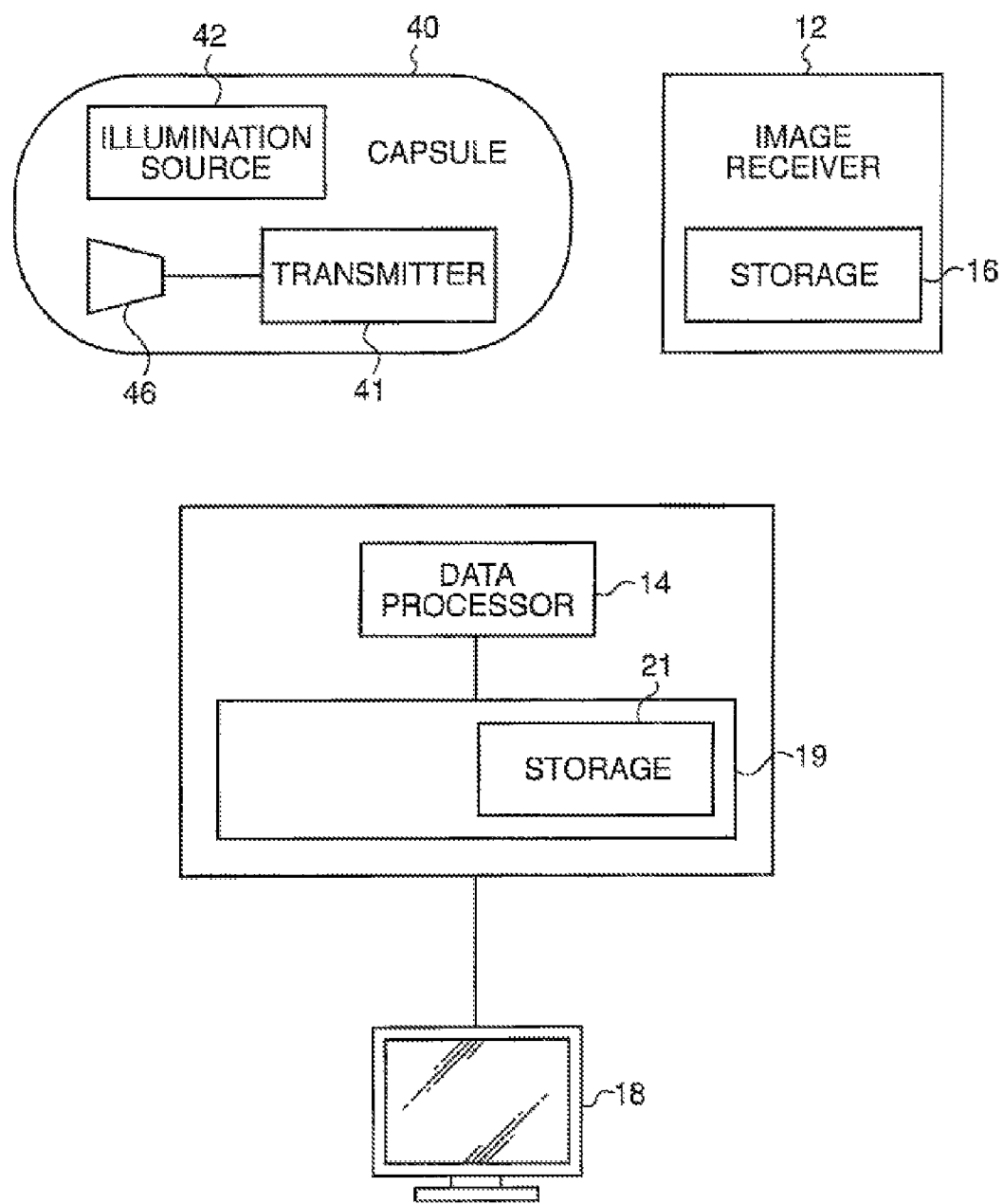
FIG. 1 shows a schematic diagram of an in-vivo imaging system according to one embodiment of the present invention.

Reference is made to FIG. 1, which shows a schematic diagram of an in-vivo imaging system according to one embodiment of the present invention. In an exemplary embodiment, the system comprises a capsule 40 having an imager 46, for capturing images, an illumination source 42, for illuminating the body lumen, and a transmitter 41, for transmitting image and possibly other information to a receiving device. Typically, the image capture device may correspond to embodiments described in U.S. Pat. No. 5,604,531 to Iddan et al., and to embodiments described in published application WO01/65995 to Glukhovsky et al., but in alternate embodiments may be other sorts of image capture devices. The images captured by the imager system may be of any suitable shape including for example circular, square, rectangular, or hexagonal, etc. Typically, located outside the patient's body in one or more locations are an image receiver 12, typically including an antenna or antenna array (not shown), an image receiver storage unit 16, a data processor 14, a data processor storage unit 19, and an image monitor 18, for displaying, inter alia, images recorded by the capsule 40. Typically, data processor storage unit 19 includes an image database 21.

Typically, data processor 14, data processor storage unit 19 and monitor 18 are part of a personal computer or workstation, which includes standard components such as processor 14, a memory, a disk drive, and input-output devices, although alternate configurations are possible. Data processor 14 may include any standard data processor, such as a microprocessor, multiprocessor, accelerator board, or any other serial or parallel high performance data processor. Data processor 14 typically, as part of its functionality, acts as a controller controlling the display of the images. Image monitor 18 is typically a conventional video display, but may, in addition, be any other device capable of providing image or other data. The image monitor 18 presents the image data, typically in the form of still and moving pictures, and in addition may present other information. In an exemplary embodiment, the various categories of information are displayed in windows. Multiple monitors may be used to display image and other data.

In operation, imager 46 captures images and sends data representing the images to transmitter 41, which transmits images to image receiver 12 using, for example, electromagnetic radio waves. Image receiver 12 transfers the image data to image receiver storage unit 16. After a certain period of time of data collection, the image data stored in storage unit 16 is sent to the data processor 14 or the data processor storage unit 19. For example, the image receiver 12 or image receiver storage unit 16 may be taken off the patient's body and connected to the personal computer or workstation which includes the data processor 14 and data processor storage unit 19 via a standard data link, e.g., a serial, parallel, USB, or wireless interface of known construction. The image data is then transferred from the image receiver storage unit 16 to an image database 21 within data processor storage unit 19. Typically, the image stream is stored as a series of images in the image database 21, which may be implemented in a variety of known manners. Data processor 14 may analyze the data and provide the analyzed data to the image monitor 18, where a user views the image data. Data processor 14 operates software (not shown) that, in conjunction with basic operating software such as an operating system and device drivers, controls the operation of data processor 14. Typically, the software controlling data processor 14 includes code written in the C++ language, but may be implemented in a variety of known methods. Data processor 14 may include graphics software or hardware.

The image data collected and stored may be stored indefinitely, transferred to other locations, or manipulated or analyzed. A health professional may, for example, use the images to diagnose pathological conditions of the GI tract, and, in addition, the system may provide information about the location of these pathologies. While, using a system where the data processor storage unit 19 first collects data and then transfers data to the data processor 14, the image data is not viewed in real time, other configurations allow for real time viewing.

Typically, the in-vivo imager system collects a series of still images as it traverses the GI tract. The images may be later presented as a stream of images of the traverse of the GI tract. The in-vivo imager system may collect a large volume of data, as the capsule 40 may take several hours to traverse the GI tract, and may record images at a rate of, for example, two images every second, resulting in the recordation of thousands of images. The image recordation rate (or frame capture rate) may be varied.

Typically, the image data recorded and transmitted by the capsule 40 is digital color image data, although in alternate embodiments other image formats may be used. In an exemplary embodiment, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel is recorded by a one byte (i.e., 0-255) brightness value. Typically, images are stored sequentially in data processor storage unit 19. The stored data is comprised of one or more pixel properties, including color and brightness. Other image formats may be used.

Typically, data processor storage unit 19 stores a series of images recorded by a capsule 40. The images the capsule 40 records, for example, as it moves through a patient's GI tract may be combined consecutively to form a series of images displayable as an image stream. When viewing the image stream, the user is typically presented with one or more windows on monitor 18; in alternate embodiments multiple windows need not be used and only the image stream is displayed. In an embodiment where multiple windows are provided, for example, an image window may provide the image stream, or still portions of that image. Another window may include buttons or other controls that may alter the display of the image; for example, stop, play, pause, capture image, step, fast-forward, rewind, or other controls. Such controls may be activated by, for example, a pointing device such as a mouse or trackball. Typically, the image stream may be frozen to view one frame, speeded up, or reversed; sections may be skipped; or any other method for viewing an image may be applied to the image stream.

While the following discussion relates to the case where data from a capsule 40 is stored for later use, the system and method of the present invention may be used with systems allowing for real time viewing of image data.

While, typically, information gathering, storage and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle etc.

In another embodiment, information gathering can be performed in another cavity besides a lumen in a human body. An example can include information gathered in an animal lumen. Another example can include information gathered from pipes or other cavities formed during a manufacturing process. Yet another example can be information gathered through a natural stream, for example, geological or marine formations.

Furthermore, while typically the components accepting, processing and displaying the image data are contained within a workstation system or PC, other systems may be used, and other (e.g., distributed) components may perform such image accepting, processing and displaying.

In one embodiment, the image stream may be presented to the viewer as multiple image streams in two or more windows, such that as the image streams are displayed a set of consecutive or "nearby" frames are displayed substantially simultaneously. For example, in one embodiment, two windows or viewing areas are displayed, each displaying one frame of an image stream. Typically, the frames are displayed substantially simultaneously. According to one embodiment, in each time slot, two images which are consecutive in the image stream are displayed, one in each window or viewing area. For example, in one embodiment, the image stream is divided into two separate streams that are displayed substantially simultaneously. Frames, which are consecutive or adjacent in the original stream, become in the separate streams, corresponding frames (e.g., the first frame in each corresponding stream, the second frame in each corresponding stream). Thus, when the two resulting streams are displayed, frames 1 and 2 from the original stream may be displayed side by side, then frames 3 and 4, etc. In another embodiment the image stream is divided into three or more separate streams that are displayed substantially simultaneously. In yet another embodiment some frames in the stream may be skipped.

In an exemplary embodiment, the windows or viewing areas are close together, with a minimum of blank or black space between the images, and typically horizontally and side by side, to allow a viewer to see the entirety of the images without substantially moving his eyes. The images may be distorted (e.g., displayed in a cone, oval or ellipse shaped field) to further reduce the space between them. The images may be displayed with symmetry. For example, the images may be displayed in the same horizontal plane. One image may be reversed and presented as a mirror image, the images may have their orientation otherwise altered, or the images may be otherwise processed to increase symmetry.

Typically, if normally the image stream is displayed at a certain rate, the two separate image streams displayed according to one embodiment may each be displayed at half that speed. Thus, if the image stream may be displayed at 20 frames per second each of the two streams may be displayed at 10 frames per second. In such a case the same number of overall frames per second is displayed, but the user can view twice as much information for twice as long. The total display time for the image streams is the same as that of the original image stream, but each frame is displayed to the user for a longer period of time. In another example, if a user is comfortably viewing a single image stream at one rate, adding a second stream will allow the user to increase the total review rate without reducing the time that each frame is displayed. In alternate embodiments, the relationship between the display rate when the image stream is displayed as one image stream and when it is displayed as multiple streams may differ; for example, the resulting multiple image streams may be displayed at the same rate as the original image stream.

Figure 2:
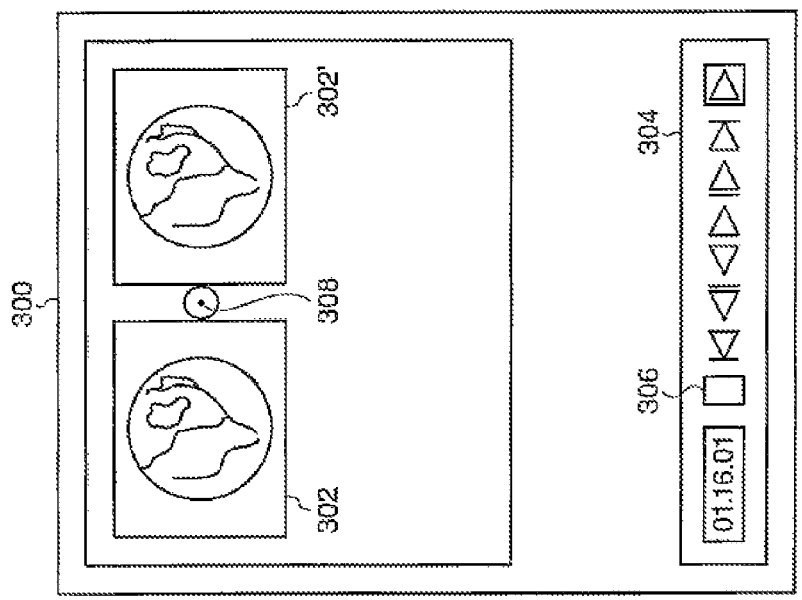
FIG. 2 depicts a portion of a display according to an embodiment of the present invention.

In an exemplary embodiment, the user may switch modes, between viewing the images as one stream and viewing the images as multiple streams using a control such as a keystroke or on-screen button. The user may control the multiple streams in a manner similar to the control of a single stream, for example by using on screen controls. In an alternate embodiment, only one mode may be offered to the user. FIG. 2 depicts a portion of a display according to an embodiment of the present invention. Referring to FIG. 2, the display 300 is in multiple image stream mode. The display 300 may be displayed on, for example, image monitor 18. Typically, the display 300 includes a set of image windows 302 and 302', for displaying image streams, and a set of controls 304. The controls 304 may include, for example, a toggle control 306, allowing the user to toggle between a multiple image stream mode and a single image stream mode. The controls 304 may also include, for example, conventional video controls, such as pause, stop, play, fast-forward, reverse, etc. In a typical embodiment, if the system is in a multiple image stream mode, the controls 304 act on all image streams simultaneously; in alternate embodiments, other methods may be used, for example the controls 304 may act on a single image stream.

As seen in FIG. 2, two image streams are displayed. Typically, at any one time, since the images in each image stream are substantially adjacent, since adjacent images are typically similar, and since each image stream is displayed synchronously (e.g., the frame having the same or similar frame number is displayed for each), the images displayed in window 302 and 302' are substantially similar. Typically, a user viewing multiple image streams directs the center of his vision to a point in-between the image streams, e.g., point 308. Typically point 308 is not displayed on the monitor 18 (but may be); point 308 is included in FIG. 2 for illustrative purposes. The user may absorb the relevant information about the image streams in such a manner; such viewing may require a period of training. For example, if the image streams are of the GI tract, the user may, by directing his gaze to point 308, absorb information regarding pathologies from the set of image windows.

In alternate embodiments, the different image streams may be placed in different configurations on a viewing screen. For example, rather than horizontally, the image streams may be arranged vertically or diagonally. In further embodiments, different numbers of image streams may be displayed. For example, if three image streams are to be displayed simultaneously, frames 1, 2 and 3 of the original stream may be displayed, then frames 4, 5 and 6, etc. In further embodiments, adjacent frames need not be displayed, and the frames may not be displaying the specific patterns discussed herein. For example, certain frames may be skipped: frames 1 and 6 may be displayed, then frames 3 and 8, etc. Frames that are substantially adjacent, rather than immediately adjacent (e.g., frames 1 and 5), may be displayed simultaneously. The frames in different image streams need not be displayed simultaneously; the frames may be displayed at different times or independently.

Various methods may be used to separate an original image stream into one or more secondary image streams to be displayed. In one embodiment, images from the original image are simply directed to the proper screen position at viewing time, and the image stream is not actually separated; in alternate embodiments, the images may be separated for example, placed in different files or memory blocks. In one embodiment, each resulting image stream includes a separate subset of images from the original image stream; in alternate embodiments, the images from each resulting image stream may overlap. Subset image streams may include different images from the original stream in different embodiments.

In certain embodiments of the present invention, more than one image stream may be collected. For example, an in-vivo vehicle may include more than one imager (or one imager) collecting multiple image streams—possibly by including an imager or lens system in more than one location on the vehicle. Capsule 40 may include more than one imager 46. The imagers 46 may be arranged, for example, at either end of the capsule 40, or at the same end of the capsule, in slightly different positions or different angles. A capsule which includes a plurality of imagers is described, for example, in International Publication Number WO 02/054932 which is assigned to the common assignee of the present application. Each imager 46 may capture images and transmit the images via the transmitter 41 or via separate transmitters. Typically, each imager 46 has associated an optical system. In such a case, an embodiment of the system and method of the present invention may display each image stream simultaneously, where each image displayed on the viewer screen was typically captured at the same time. In one embodiment, images from each of the imagers can be displayed substantially simultaneously so that image streams from different imagers can be reviewed simultaneously. In another embodiment, image streams from each imager may be divided into a number of subset image streams and the subset image streams for one or more imagers may be shown substantially simultaneously. E.g., one subset image stream may include every other image frame whereas the second subset stream may include every other consecutive image frame (e.g. the first subset includes frames 1,3,5 etc and the second subset includes frames 2,4,6 etc.). Typically, in such a case images may be shown in matrix form so that each column may display frames from a single imager and each row may display frames from a different imager. Alternatively, each row may display frames from a single imager and each column may display frames from a different imager. In further embodiments, an image stream may be divided up or partitioned into sections, rather than based on substantially adjacent frames. For example, an image stream may be divided into a first section and a second section, where the first and second section are sequential. The two sections may be displayed simultaneously. More sections or partitions may be created.

Figure 3:
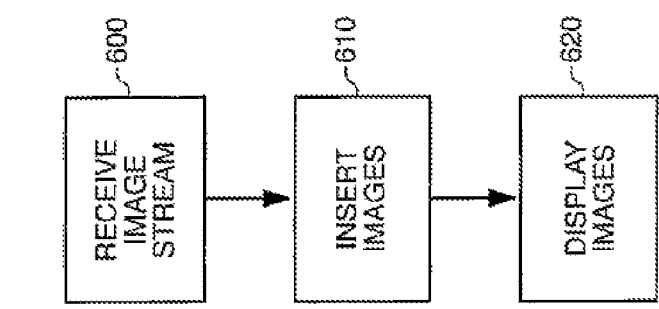
FIG. 3 is a flow chart of a method for viewing an image stream according to an embodiment of the invention.

According to an embodiment of the invention a method for viewing an image stream includes the step of displaying an original image stream as a plurality of image streams. Reference is now made to FIG. 3, which schematically illustrates a method according to one embodiment of the invention. According to one embodiment an original stream of images is obtained (step 310), for example, by using images obtained by an imaging capsule that traverses the GI tract while acquiring images of the GI tract. The original image stream is then divided into a plurality of subset image streams (step 320), each subset including at least a portion of the original image stream. According to one embodiment, frames, which are consecutive or adjacent in the original stream, become in the separate streams, corresponding frames (e.g., the first frame in each corresponding stream, the second frame in each corresponding stream). Thus, when the two resulting streams are displayed, frames 1 and 2 from the original stream may be displayed side by side, then frames 3 and 4, etc. The subset streams are displayed on a display (step 330) preferable substantially simultaneously, typically for observing and/or analyzing, for example, for detecting pathologies in the GI tract. In one embodiment of the invention, the main display engine is programmed to select the next two images to be displayed substantially at the same time (instead of the next image), and a display window displays those two images at the substantially the same time, until the next two images are selected from the display engine.

In an exemplary embodiment, the windows or viewing areas are close together, with a minimum of blank or black space between the images, and are typically horizontally and side by side, to allow a viewer to see the entirety of the images without substantially moving his eyes. The images may be distorted (e.g., displayed in a cone, oval or ellipse shaped field) to further reduce the space between them. The images may be displayed with symmetry. For example, the images may be displayed in the same horizontal plane. One image may be reversed and presented as a mirror image, the images may have their orientation otherwise altered, or the images may be otherwise processed to increase symmetry. Typically, a tool available to the user which manipulates an image (e.g., region of interest or zoom) will have an identical effect on all images simultaneously displayed. Each image may be displayed with different post-processing. For example, one image may be subject to certain filtering or manipulation (e.g., red or green filtering, contrast enhancement, brightness alteration) and the other image may be subject to different or no filtering or manipulation.

In one embodiment two or more images in a stream or in a plurality of streams displayed substantially simultaneously are fused together and displayed as a single entity. As such, a user may comfortably and concurrently incorporate information shown in each of the images while avoiding the distraction caused by the typically sharp contrast between connecting edges or between the images and the background color which may appear between the images when the images are spaced apart.

According to some embodiments fusing of independent images may be accomplished by, for example, one or more post processing algorithms known in the art, including but not limited to, smoothing convolution, mirroring, overlapping, linear or non-linear fade-out fade-in, truncation, linear shape distortion, non-linear shape distortion, normalization or intensity, or other suitable post-processing.

In one embodiment, a relative position for two or more images may be defined, and juxtaposed edges of images may be defined. A smoothing convolution on the juxtaposed edges may be performed, and the images may be displayed with the smoothing convolution. A fade-out in intensity may be performed substantially near the juxtaposed edges, and the images may be at least partially overlapped to obtain an overlapping region. In one embodiment, the overlapping region may be defined as a sum of juxtaposed edges, and the intensity in the overlapping region may be normalized. The juxtaposed edges may be mirrored, and a fade-out in intensity on the mirroring regions may be performed, obtaining faded-out mirroring regions.

Figure 4A:
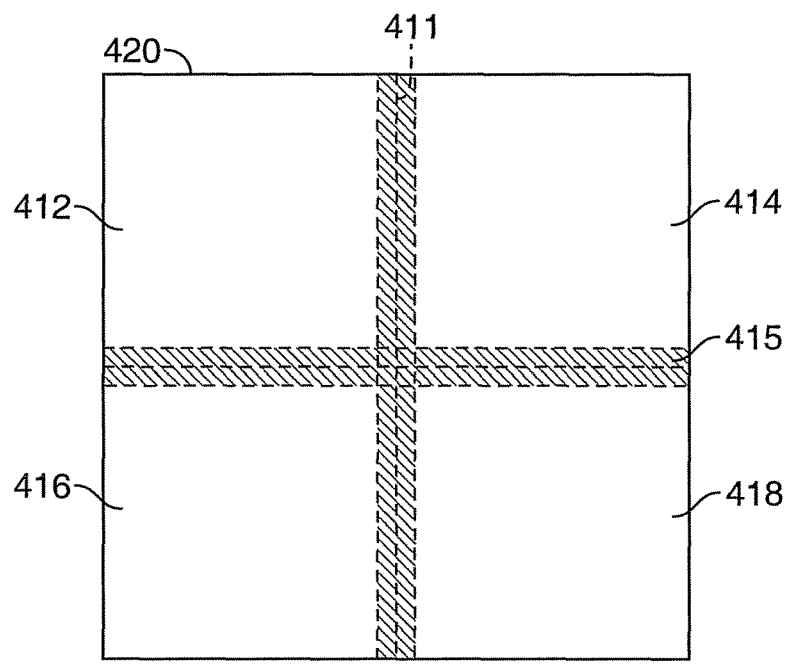
FIG. 4A is a schematic depicting a method of generating a single image from four square images according to an embodiment of the invention.
Figure 5A:
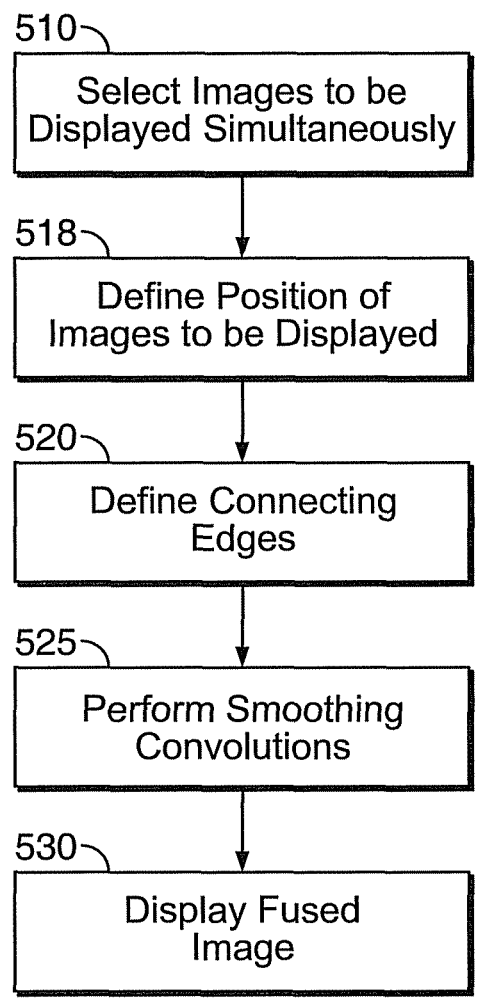
FIG. 5A is a flow chart depicting a method for generating a single image from four square images according to an embodiment of the invention.

Reference is now made to FIG. 4A, a schematic showing how a new image 420 may be generated from original images 412, 414, 416, and 418 displayed substantially simultaneously, according to one embodiment of the invention. Images 412, 414, 416, and 418 are fused to each other to form a larger square. In one embodiment, post processing is performed over a predefined area 415 around the touching edges, for example touching edge 411 between original images 412 and 414. In other embodiments post processing may be performed on all the original images in their entirety. In yet another embodiment, no post-processing is performed. FIG. 5A describes an algorithm that may be used in one embodiment of the invention. In step 510, the images to be displayed substantially simultaneously are selected. This step may include selecting the number of images to be displayed substantially simultaneously from a stream of images when images are displayed chronologically, selecting the number of images from more than one stream of images, and/or selecting images from a stream or a subset stream of images based on other criteria for example based on spectral characteristics of images (e.g. intensity, saturation, hue, etc). In step 515, the position of the images used to form a fused image in a defined geometrical shape (eg. square, rectangle, cross, etc.) is defined. Based on the positioning of each image, the at least partially connecting edges between two substantially juxtaposed images are defined in step 520. Smoothing convolution is performed on defined connecting edges in step 525 and the resultant fused image is displayed in step 530. In another embodiment of the invention, smoothing convolution is not performed. Other algorithms besides and in addition to smoothing convolution may be used as well including mirroring, overlapping, linear or non-linear fade-out fade-in, truncation, etc. In another embodiment of the invention, post-processing algorithms need not be used.

Figure 4B:
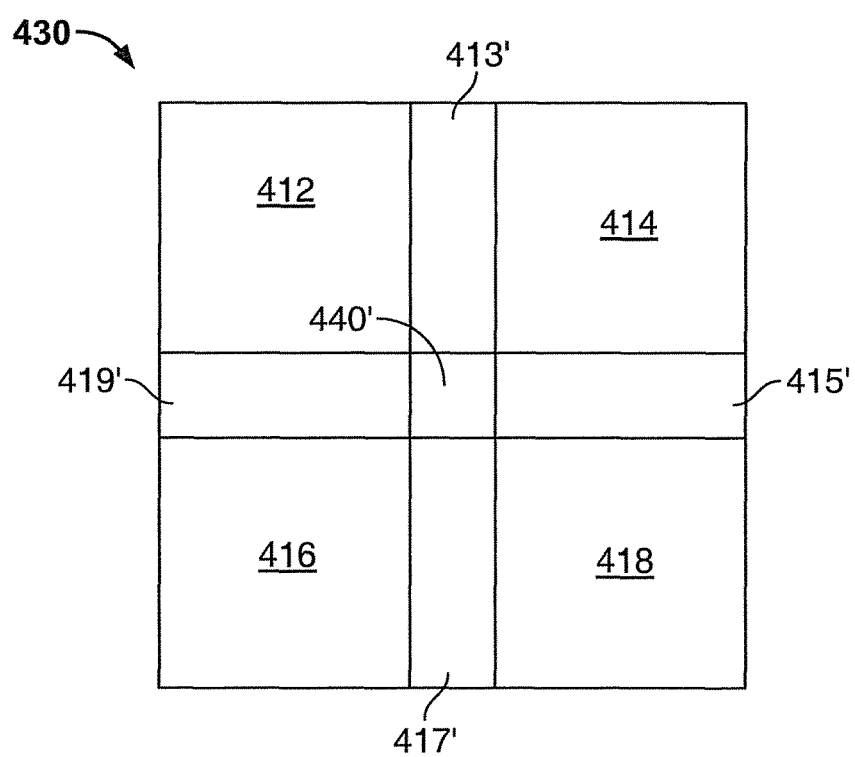
FIG. 4B is a schematic depicting a method of generating a single image from four square images according to another embodiment of the invention.
Figure 5B:
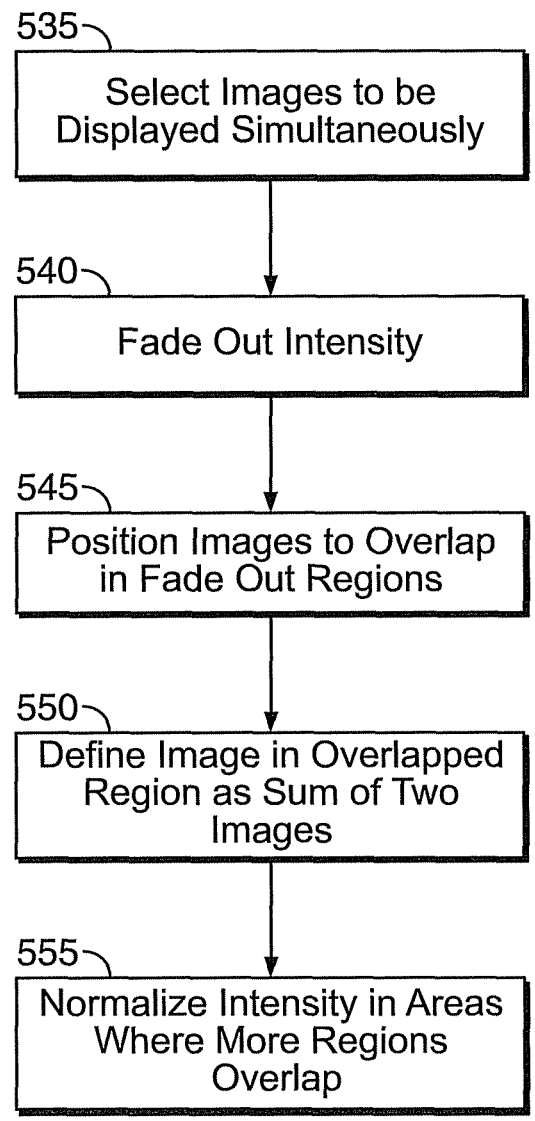
FIG. 5B is a flow chart depicting a method for generating a single image from four square images according to another embodiment of the invention.

FIG. 4B is a schematic showing how a new image 430 may be generated from original images 412, 414, 416, and 418 displayed substantially simultaneously in one embodiment of the invention. Images 412, 414, 416, and 418 are partially overlapping to form a larger square. In one embodiment, post processing is performed in overlapping regions 413', 415', 417', 419', 440'. FIG. 5B shows an alternate algorithm where images are positioned to overlap, according to an embodiment of the invention. In this exemplary algorithm, images are selected in step 535, for example, as described above. A fade-out in intensity is performed on edges in step 540. Images are positioned so that fade-out regions overlap in step 545. The overlapped regions are defined as the sum of the two overlapped images (step 550). Normalization on the intensity is performed, for example, in region 440', where more than two overlapping regions are summed to define an area (step 555). According to other embodiments other algorithms may be used.

Figure 4C:
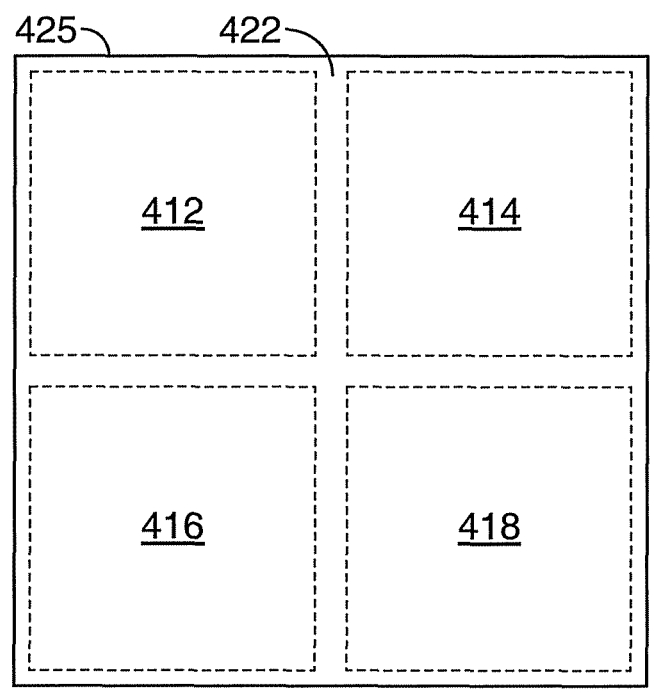
FIG. 4C is a schematic depicting a method of generating a single image from four square images according to yet another embodiment of the invention.
Figure 5C:
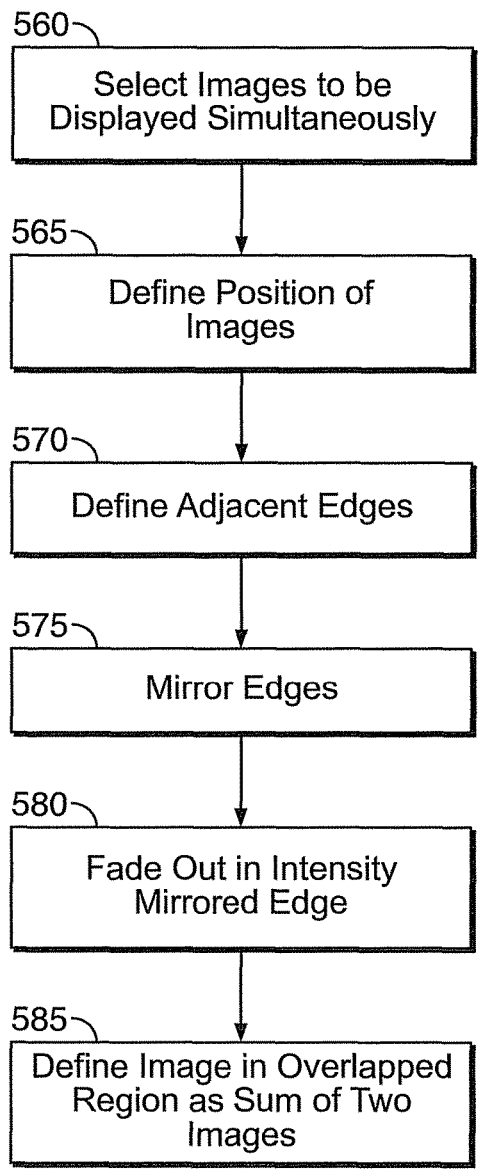
FIG. 5C is a flow chart depicting a method for generating a single image from four square images according to yet another embodiment of the invention.
Figure 6:
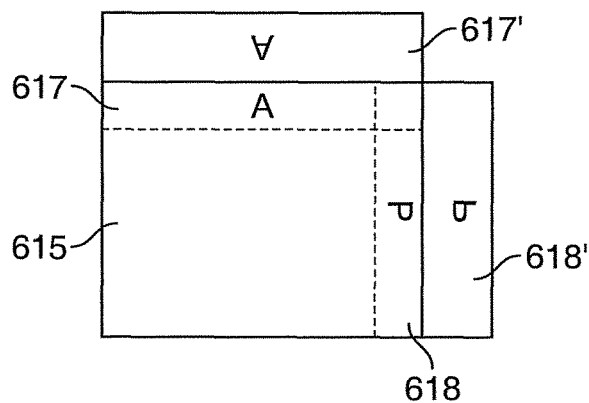
FIG. 6 is a schematic depicting technique for mirroring edges of images.

FIG. 4C, is a schematic showing how a new image 425 may be generated from four images 412, 414, 416, and 418 positioned substantially close to each other and separated by space 422, according to an embodiment of the invention. In one embodiment, original images 412, 414, 416, and 418 may stay intact so that no information is lost and area 422 is filled based on post processing performed on image content proximal to area 422. In another embodiment, when the juxtaposed images are positioned with a space between them (e.g., a pre-defined space, or another space), a background color may be used to reduce the contrast between the parallel running images. The background color may be a solid color or a stream of colors. The background color may be a stream of colors that gradually changes from the colors appearing on one edge of a first image to the colors appearing on the juxtaposed edge of a second image. In another embodiment the edges of the images are also processed such as smoothed. Other methods may be used such as mirroring of images. FIG. 6 shows an image 615 with edges 617 and 618 where mirrored edges 617' and 618' were generated. FIG. 5C describes an exemplary algorithm incorporating mirroring that may be used in one embodiment of the invention. Images to be displayed substantially simultaneously are selected in step 560, for example as described above. Position of each image is defined such that the distance between substantially juxtaposed images equals the width of the mirrored edges (step 565). The juxtaposed edges are defined (step 570) and are mirrored (step 575). Fade-out in intensity is performed on mirrored edges (step 580). The area between original images is defined as the sum of overlapping mirrored edges (step 585). A space between two or more images may be filled with one or more colors.

Figure 7A:
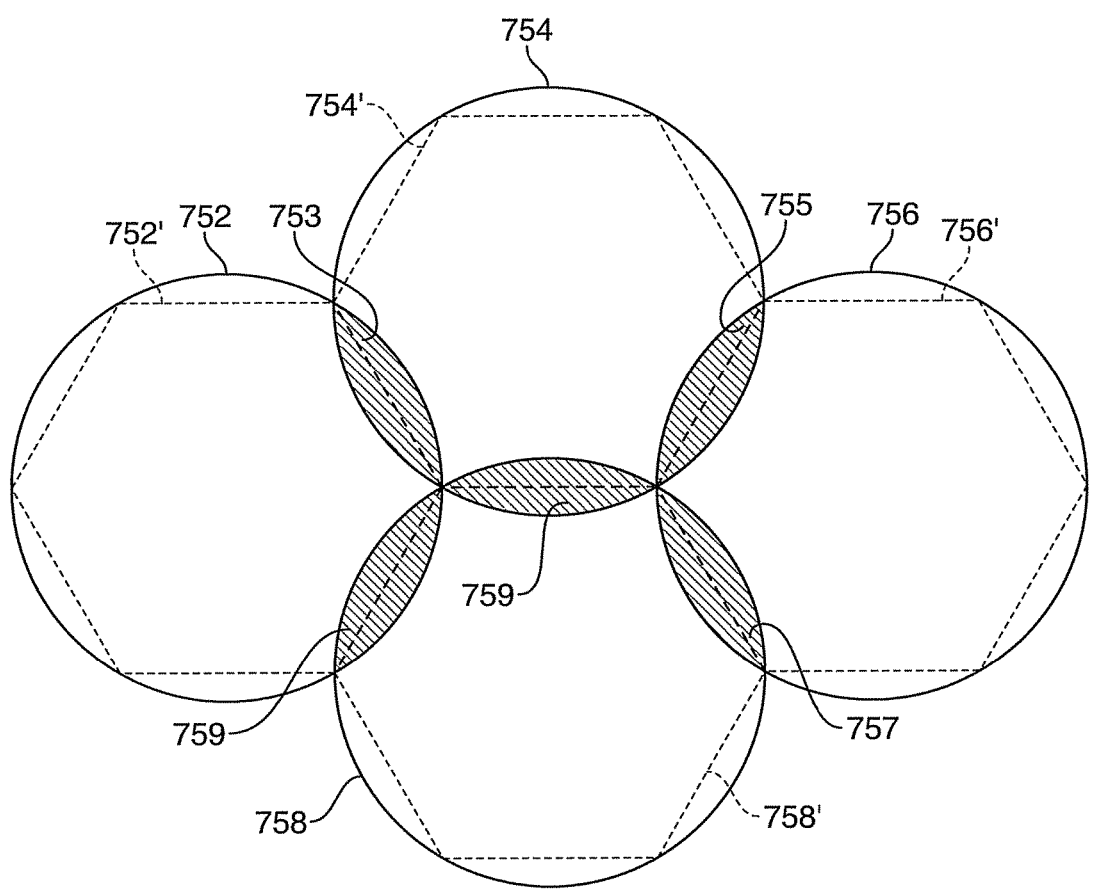
FIG. 7A is a schematic depicting a method of generating a single image from four circular images according to an embodiment of the invention.

FIGS. 4A, 4B, and 4C show exemplary embodiments using four original images to form one new image, however, more or less than four original images displayed substantially simultaneously may be used to generate a new image. The new image in one embodiment of the invention may be generated from more than four images. Original images may be of a shape other than square for example circular, rectangular, or hexagonal. FIG. 7A shows a schematic of four circular images 752, 754, 756, and 758. Images 752, 754, 756, and 758 are positioned such that defined hexagonal areas 752', 754', 756', and 758' inside corresponding circular images have touching edges, for example touching edge 759 between hexagonal area 754' and 758'. As such overlapping areas 753, 755, 757, and 759 are created. In this embodiment of the invention post processing may be performed over overlapping areas 753, 755, 757, and 759 to create a new image incorporating original images 752, 754, 756, and 758.

Figure 7B:
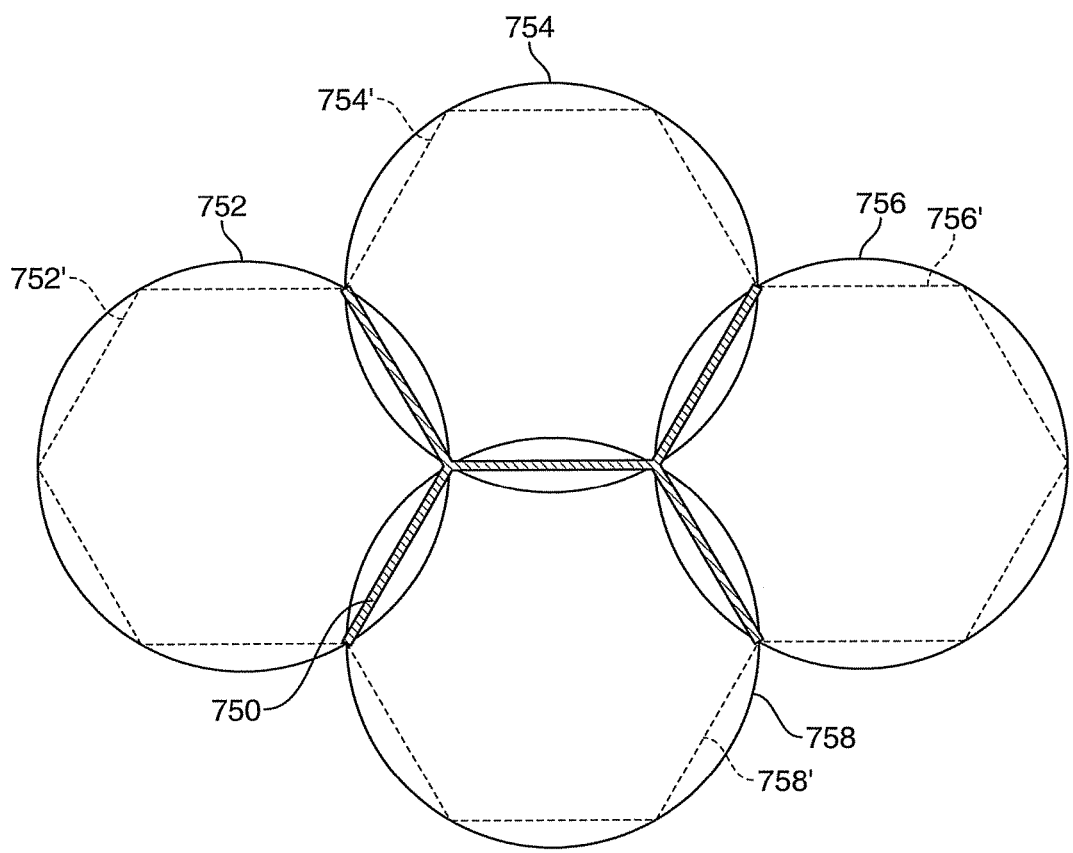
FIG. 7B is a schematic depicting a method of generating a single image from four circular images according to another embodiment of the invention.

FIG. 7B shows an alternate embodiment where circular images 752, 754, 756, and 758 are positioned such that defined hexagonal areas 752', 754', 756', and 758' inside corresponding circular images would have over lapping area 750 around the touching edges. In this embodiment, post processing may be performed, for example on overlapping area 750.

Figure 8:
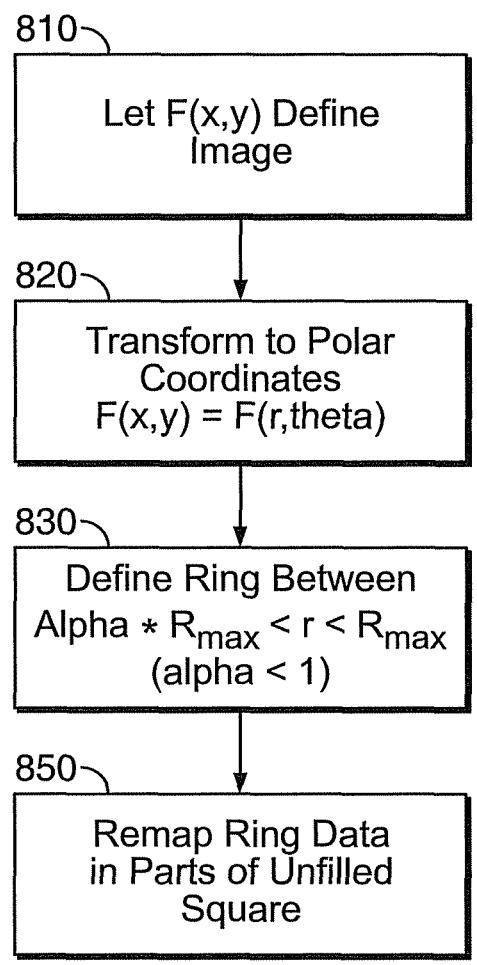
FIG. 8 is a flow chart depicting a method for generating a square image from an originally circular image.

In an alternate embodiment when working with circular images, loss of information due to truncation or overlapping may be reduced or all together prevented by distorting the original circular image into an alternate shape such as for example a square, hexagon, octagon, sector, or any other symmetrical or non-symmetrical shape. FIG. 8 describes an exemplary algorithm of how a square image may be generated from an originally circular image using non-linear shape distortion. In block 810 a circular image is defined by a function F(x,y) in Cartesian coordinates. The function is transformed into polar coordinates F(r, theta) in block 820. A ring along the outer perimeter of the circle is defined in block 830. The image data contained in the ring is remapped to in parts of an unfilled square in order generate a square perimeter in block 850. As such the central part of the image stays in tact and only a defined perimeter is distorted to generate a desired shape. Other shapes may be generated by partially distorting an originally circular image using this method.

Figure 9A:
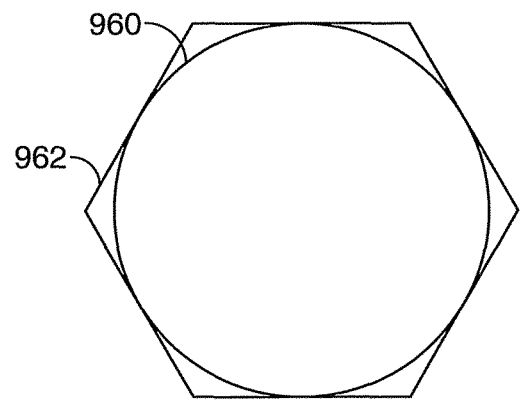
FIG. 9A is a schematic depicting shape distortion to generate a hexagonal image from an originally circular image, according to an embodiment of the invention.
Figure 9B:
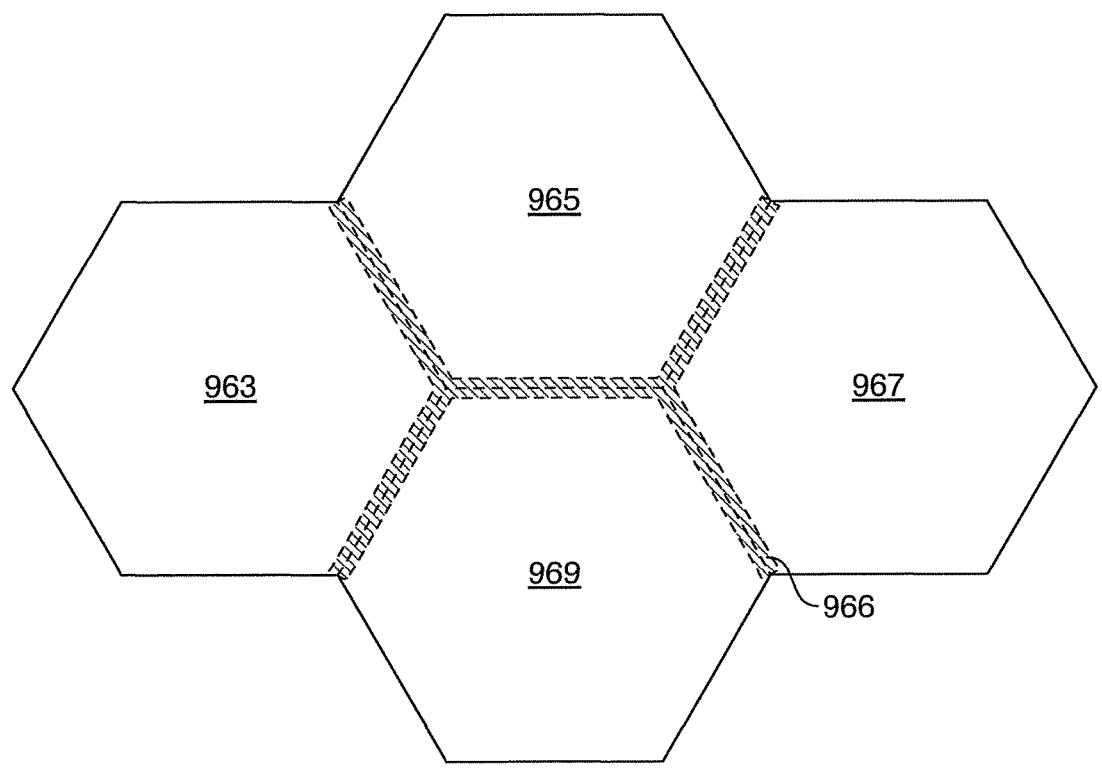
FIG. 9B is a schematic depicting a method of generating a single image from four hexagonal images according to an embodiment of the invention.

In another embodiment of the invention linear distortion is accomplished by defining an array of image data along a radius and re-mapping the array of image data along the direction of the defined radius. This method of distortion may be performed at every angle or at some range of angles of the originally circular image in order to generate an image with an alternate shape. In some embodiments an originally circular image may be almost fully distorted. Other methods may be used as well. In one embodiment of the invention, an original circular image is distorted into a hexagonal shape as is shown, for example, in FIG. 9A. Original circular image 960 may be stretched and distorted to generate a larger hexagonal image 962. FIG. 9B shows an example of four juxtaposed hexagonal images 963, 965, 967, and 969 distorted from originally circular images. Images 963, 965, 967, and 969 may be used to create a single image by, for example, smoothing in the area near the touching edges for example touching edge 966. In another embodiment of the invention, a hexagon may be truncated from an originally square, circular, or rectangular image. In yet another embodiment of the invention, a new image is generated from substantially more than four hexagonal images positioned in a honeycomb structure. Distortion may be performed along the entire perimeter of the originally circular image 960, such as in distorted image 962 or in an alternate embodiment, partial distortion may be performed (not shown) for example distortion to generate one or more sides of a hexagon.

Figure 10A:
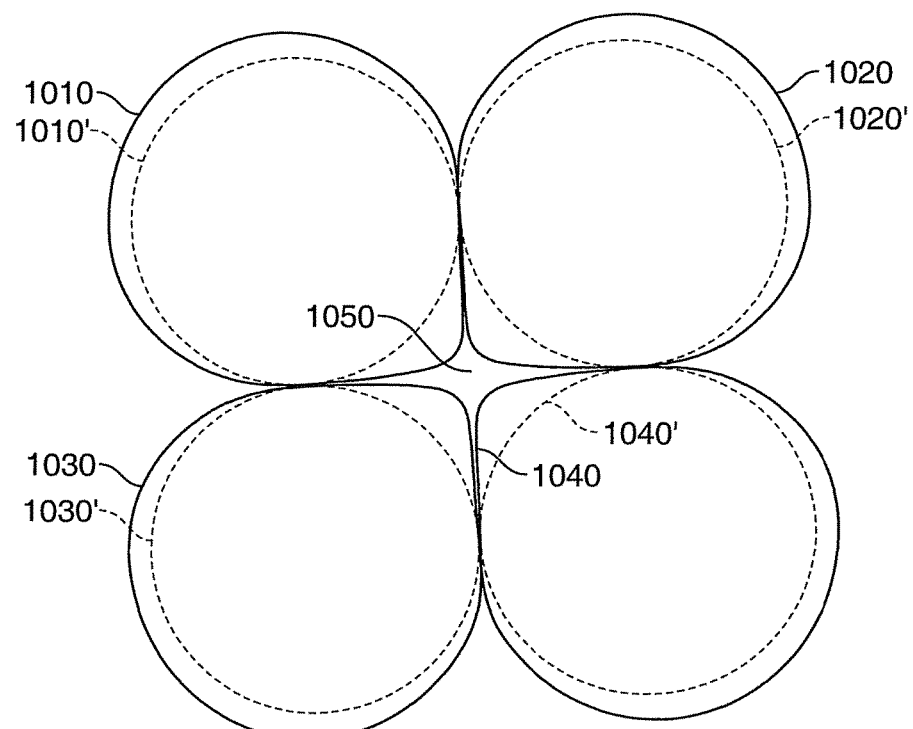
FIG. 10A is a schematic depicting a method of distorting originally circular images according to an embodiment of the invention.

In another embodiment of the invention, images may be distorted to shapes other than square or hexagonal. For example, an originally circular image may be distorted to an octagon, a sector or near sector shape or to any other symmetrical or non-symmetrical shape. Distortion may or may not include truncation, smoothing convolution, re-mapping or any other method known in the art. FIG. 10A shows four exemplary juxtaposed images 1010, 1020, 1030, and 1040 that were distorted from originally circular images 1010', 1020', 1030', and 1040'. In this exemplary embodiment, the image distortion moves the image data toward dead space 1050 that is also the center of view. The originally circular images 1010', 1020', 1030', and 1040' are zoomed in the periphery as well so as to create emphasis in the area away from the center of view. Smoothing convolution, mirroring, overlapping, linear or non-linear fade-out fade-in, truncation, or any of the methods described above may be used to fuse the distorted images 1010, 1020, 1030, and 1040 once formed. The resultant fused image in this exemplary embodiment is a flower shaped image, but may have other shapes (e.g., honeycomb, etc.).

Figure 10B:
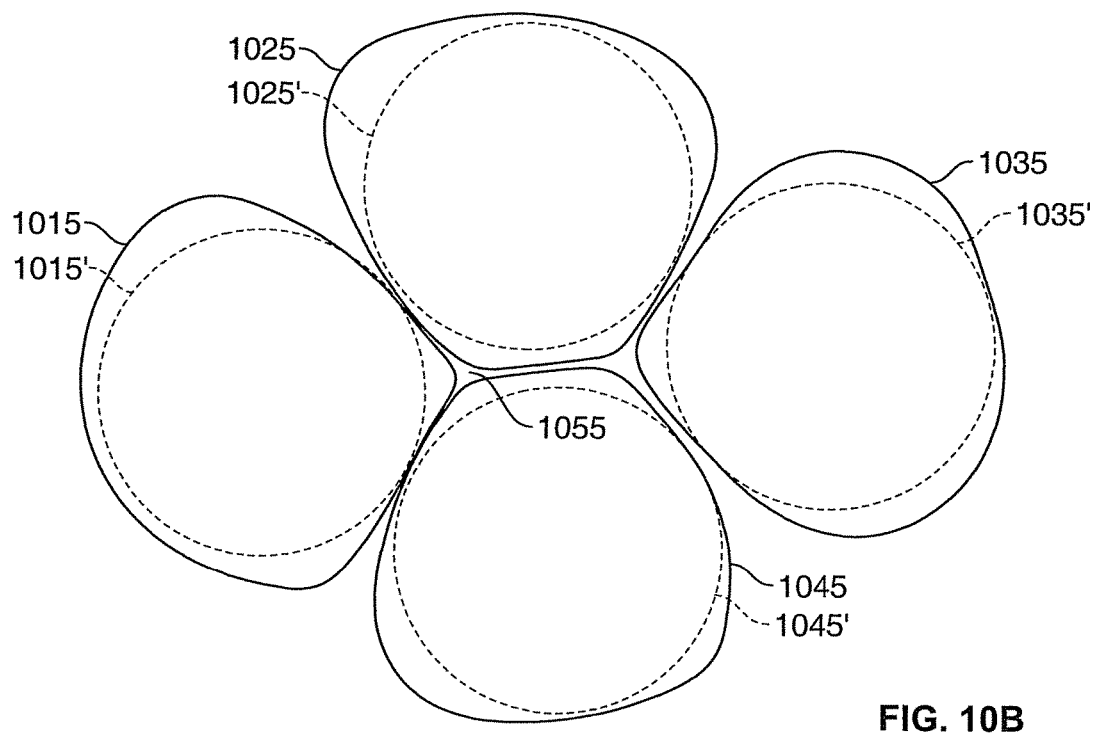
FIG. 10B is a schematic depicting a method of distorting originally circular images according to another embodiment of the invention.

In another exemplary embodiment shown in FIG. 10B four juxtaposed images 1015, 1025, 1035, and 1045 are arranged in an oblong fashion. In this exemplary embodiment, the distorted images 1025 and 1045 generated from the originally circular images 1020' and 1045' are of a different shape than the distorted images 1015 and 1035 generated from the originally circular images 1015' and 1035'. In this exemplary embodiment the image distortion serves to move the image data toward the dead space 1055 that is also the center of view. The originally circular images 1015', 1025', 1035', and 1045' are zoomed in the periphery as well so as to create emphasis in the area away from the center of view. Smoothing convolution, mirroring, overlapping, linear or non-linear fade-out fade-in, truncation, or any of the methods described above may be used to fuse the distorted images 1015, 1025, 1035, and 1045. The resultant fused image in this exemplary embodiment is a flower shaped image.

Images displayed substantially simultaneously may be a subset of images taken from a single stream of images or from more than one stream of images. Images displayed substantially simultaneously may be sequential images in a stream based on chronological order or may be arranged in another order. In one embodiment images displayed substantially simultaneously may be selected based on spectral characteristics of each image displayed, for example intensity, hue, etc. More than one characteristic may be used to determine the order or positioning of the images displayed substantially simultaneously. For example, within a certain time frame, images from a stream may be selected to belong to a specific subgroup displayed substantially simultaneously based on minimal color variance. The larger image generated from two or more images may be streamed like a video where images are replaced at some given frequency or may be scrolled to move horizontally or vertically across the monitor.

In one embodiment the user can select the number of images incorporated in the larger image, the frequency at which the image is updated, and the type of viewing (e.g. video, horizontal scrolling, vertical scrolling, etc.).

In another embodiment a still image can be displayed substantially juxtaposed to the image streams so that the image streams can be easily compared to the still image during the viewing process. In yet another embodiment, an image stream obtained form an imager is displayed substantially simultaneously and substantially juxtaposed to an image stream obtained from an ultrasound, temperature and/or a pH imager. Displaying image streams or single images substantially simultaneously, from different types of imagers may help to draw a users attention to frames that may show abnormalities and/or pathologies.

In alternate embodiments, the system and method of the present invention may operate on image streams having alternate formats, on image streams being from alternate sources than a capsule, and containing images from sites other than the GI tract.

Embodiments of the present invention may allow an image stream to be viewed as a smoother moving image, with less jitter by reducing the rate at which each image in the set of images displayed substantially simultaneously are streamed, without decreasing the original stream rate. In some cases, if concurrently displayed images differ in a certain manner, the viewer may be able to more easily spot pathologies or other conditions.

In one embodiment of the system and method of the present invention, an image stream is displayed to the user in a manner reducing jitter, smoothing the presentation, and allowing easier and more pleasant viewing of the image stream. In such an embodiment, additional intermediate images are formed and inserted into the image stream, the intermediate images being formed from combinations of adjacent or substantially adjacent images. In one embodiment, the combinations are created by morphing or averaging adjacent images so that the resulting additional image is, when viewed as part of a moving image stream, somewhere intermediate in time to the two original images. In alternate embodiments other methods of combining images may be used. In one embodiment, synthesizing methods such as those used in the MotionPerfect® software provided by DynePel of Germany may be used. Such methods use motion information from the moving image stream to interpolate data for additional image frames. Other interpolation or synthesizing methods may be used.

The system and method of the present invention may allow an image stream to be viewed in an efficient manner and over a shorter time period.

It will be appreciated by persons skilled in the art that the present invention is not limited by what has been particularly shown and described hereinabove.

Rather the scope of the invention is defined by the claims that follow:

1. A method for displaying an image stream obtained from a swallowable capsule, the method comprising:
   receiving consecutive images which are consecutive within an original image stream;
   across a plurality of consecutive time slots:
      during each single time slot displaying to a viewer a plurality of images which are consecutive within the original image stream at the same time within the single time slot, each image of the plurality of consecutive images being displayed to the viewer at the same time as each other image of the plurality of images,
      the plurality of consecutive images displayed to the viewer in each time slot being immediately consecutive, in the original image stream, to the plurality of consecutive images in the immediately previous time slot, and
   wherein in each time slot a plurality of images is arranged for display such that the images are distorted to reduce the space between them.

2. The method according to claim 1 wherein distorting comprises transforming the images from a first shape to an alternate shape.

3. The method according to claim 1 wherein distorting comprises transforming the images to a hexagonal shape.

4. The method according to claim 1 comprising post-processing images displayed in a single time slot, wherein post-processing comprises smoothing, mirroring, overlapping, fade-out, fade-in, truncation, or normalization of intensity.

5. The method according to claim 1 comprising filling the space between images based on image content proximal to the space.

6. The method of claim 1, wherein the plurality of images are arranged so that they are positioned substantially close to each other.

7. A system for displaying an image stream obtained from a swallowable capsule, the system comprising:
   a memory; and
   a processor to:
      receive consecutive images which are consecutive within an original image stream;
      across a plurality of consecutive time slots, displaying to a viewer in each single time slot a plurality of consecutive images images which are consecutive within the original image stream at the same time within the single time slot, each image of the plurality of consecutive images being displayed to the viewer at the same time as each other image of the plurality of images, the plurality of of consecutive images displayed to the viewer in each time slot being immediately consecutive, in the original image stream, to the plurality of consecutive images in the immediately previous time slot, and wherein in each time slot a plurality of images is arranged for display such that the images are distorted to reduce the space between them.

8. The method according to claim 6 wherein distorting comprises transforming the images from a first shape to an alternate shape.

9. The method according to claim 6 wherein distorting comprises transforming the images to a hexagonal shape.

10. The method according to claim 6 wherein the processor is to perform post-processing on images displayed in a single time slot, wherein post-processing comprises smoothing, mirroring, overlapping, fade-out, fade-in, truncation, or normalization of intensity.

11. The method according to claim 6 wherein the processor is to fill the space between images based on image content proximal to the space.

12. The system according to claim 7, wherein the plurality of images are arranged so that they are positioned substantially close to each other.

13. A method for displaying an image stream the method comprising:
   for each of a different plurality of images in the image stream:
   arranging the plurality of consecutive images from the image stream for display to a viewer in a single time slot;
   distorting the plurality of consecutive images to reduce the space between them; and
   displaying the arranged images to the viewer in a single time slot, wherein during each time slot a plurality of images which are consecutive within the original image stream is displayed to the viewer, each image within the plurality being displayed at the same time.

* * * * *